United States Patent
Britvan (10) Patent No.: US 10,639,214 B1
(45) Date of Patent: May 5, 2020

(54) EAR CLEANING DEVICE WITH PERSONAL AND MEDICAL APPLICATOR USES

(71) Applicant: Jack J. Britvan, Jericho, NY (US)

(72) Inventor: Jack J. Britvan, Jericho, NY (US)

( * ) Notice: Subject to any disclaimer, the term of this patent is extended or adjusted under 35 U.S.C. 154(b) by 285 days.

(21) Appl. No.: 15/828,830

(22) Filed: Dec. 1, 2017

Related U.S. Application Data (63) Continuation-in-part of application No. 14/543,450, filed on Nov. 17, 2014, now abandoned.

(51) Int. Cl.
*A61F 13/38* (2006.01)
*A61F 11/00* (2006.01)

(52) U.S. Cl.
CPC ............ *A61F 13/38* (2013.01); *A61F 11/006* (2013.01); *A61M 2210/0662* (2013.01)

(58) Field of Classification Search
CPC ................................ A61F 13/38; A61F 11/006
See application file for complete search history.

(56) References Cited

U.S. PATENT DOCUMENTS

| 147,660 | A | | 2/1874 | Leiner |
| 320,889 | A | | 6/1885 | Ruoff |
| 1,652,108 | A | * | 12/1927 | Forbis ............. A61F 13/38 604/1 |
| 1,693,581 | A | | 11/1928 | Etling |
| 1,980,826 | A | | 11/1934 | Reiss |
| 2,510,961 | A | | 6/1950 | Davis |
| 2,948,280 | A | | 8/1960 | Vicik |
| 2,987,063 | A | | 6/1961 | Glickston |
| 3,203,418 | A | | 8/1965 | Johnston |

(Continued)

FOREIGN PATENT DOCUMENTS

| EP | 0 744 168 | 11/1996 |
| GB | 2 380 122 | 4/2003 |

(Continued)

OTHER PUBLICATIONS

Hearing Health & Technology Matters, Wayne's World, Tympanic Membrane—Anatomical Influence on Hearing and Fittings, Apr. 23, 2013, http://hearinghealthmatters.org/waynesworld/2013/tympanic-membrane-anatomical-influence-on-hearing-aid-fittings/.

(Continued)

*Primary Examiner* — Tatyana Zalukaeva
*Assistant Examiner* — Gabriella E Burnette
(74) *Attorney, Agent, or Firm* — Thomas A. O'Rourke; Bodner & O'Rourke, LLP (57) ABSTRACT

An ear cleaning device is configured for use on a plurality of different sized/aged persons, and includes: first and second posts, transversely disposed at substantially a 90 degree angle, being fixedly secured to each other at a selective location to be coplanar. A first end and a second end of the first post each having a swab material secured thereon to form respective first and second swab members; and a first end and a second end of the second post each having a swab material secured thereon to form respective third and fourth swab members. A length for each of the first swab member, the second swab member, the third swab member, and the fourth swab member is uniquely sized according to a distance from the pinna of the ear to the tympanic membrane, for an infant, for a toddler, for a child, and for an adult, respectively.

16 Claims, 12 Drawing Sheets

(56) References Cited

U.S. PATENT DOCUMENTS

| | | | |
|---|---|---|---|
| 3,586,380 A * | 6/1971 | Alibeckoff | A61F 13/38 300/21 |
| 3,626,946 A | 12/1971 | Messey | |
| 4,411,265 A | 10/1983 | Eichenlaub | |
| 4,457,756 A * | 7/1984 | Kern | A61B 17/12022 424/434 |
| 4,767,398 A * | 8/1988 | Blasius, Jr. | A45D 40/28 604/1 |
| 4,804,362 A | 2/1989 | Enzo | |
| 4,820,259 A * | 4/1989 | Stevens | A61F 11/00 604/1 |
| 4,902,275 A | 2/1990 | Fassbind | |
| D318,730 S | 7/1991 | Schiavo | |
| 5,107,861 A | 4/1992 | Narboni | |
| 5,120,301 A * | 6/1992 | Wu | A61M 35/006 401/132 |
| 5,127,899 A | 7/1992 | Schmerse | |
| 5,147,288 A | 9/1992 | Schiavo | |
| 5,152,742 A | 10/1992 | Simpson | |
| 5,158,532 A | 10/1992 | Peng | |
| 5,334,212 A | 8/1994 | Karell | |
| 5,509,921 A * | 4/1996 | Karell | A61B 1/227 606/162 |
| 5,632,756 A | 5/1997 | Kruglick | |
| 5,762,494 A * | 6/1998 | Archambault | A61C 19/063 424/435 |
| 5,888,199 A | 3/1999 | Karell | |
| 5,945,640 A * | 8/1999 | Rossini | A61B 7/026 181/131 |
| 6,036,385 A * | 3/2000 | Bistrack | B25G 1/102 401/48 |
| 6,080,126 A * | 6/2000 | Zygmont | A61F 13/38 600/569 |
| 6,467,982 B1 * | 10/2002 | Tsao | A61F 13/38 401/205 |
| D485,615 S | 1/2004 | Harris | |
| 6,695,802 B1 * | 2/2004 | Thompson | A61F 11/006 604/1 |
| 6,736,826 B2 | 5/2004 | Begun | |
| 7,243,577 B1 * | 7/2007 | Morris | B25B 13/463 81/124.4 |
| 7,563,239 B1 * | 7/2009 | Hudson | A61F 13/38 15/244.1 |
| 8,187,236 B1 | 5/2012 | French | |
| D701,600 S | 3/2014 | Kauffman | |
| 2003/0135228 A1 | 7/2003 | Crespo | |
| 2003/0181840 A1 * | 9/2003 | Tsaur | A61F 13/38 604/1 |
| 2003/0181933 A1 | 9/2003 | Eicoff | |
| 2003/0187469 A1 | 10/2003 | Olson | |
| 2006/0045296 A1 * | 3/2006 | Liao | A61F 13/38 381/312 |
| 2006/0156501 A1 * | 7/2006 | Grunberger | A45D 40/262 15/209.1 |
| 2007/0299457 A1 * | 12/2007 | Morales | A61F 11/006 606/162 |
| 2008/0169002 A1 * | 7/2008 | Hwang | A46B 9/021 132/320 |
| 2008/0300527 A1 * | 12/2008 | Bivins | A61F 11/006 604/1 |
| 2009/0012425 A1 * | 1/2009 | Dodge | A61B 10/0045 600/572 |
| 2009/0112241 A1 | 4/2009 | Bar | |
| 2009/0232580 A1 * | 9/2009 | Castel | A45D 34/04 401/41 |
| 2010/0042122 A1 * | 2/2010 | Shaw, Jr. | A61F 11/006 606/162 |
| 2011/0066172 A1 * | 3/2011 | Silverstein | A61F 11/006 606/162 |
| 2015/0291779 A1 * | 10/2015 | Hani | A61F 13/38 426/134 |
| 2016/0015153 A1 * | 1/2016 | Vidotto | A61F 13/38 206/232 |
| 2016/0310328 A1 * | 10/2016 | Pourbaba | A61F 13/38 |
| 2018/0228662 A1 * | 8/2018 | Glasner | A45D 44/00 |

FOREIGN PATENT DOCUMENTS

| | | |
|---|---|---|
| JP | H07194650 | 8/1995 |
| JP | 2002186568 | 7/2002 |
| NL | 2000125 | 1/2008 |
| TW | 201216928 | 5/2012 |

OTHER PUBLICATIONS

Hearing Health & Technology Matters, Wayne's World, Human Ear Canal VIII, Jul. 28, 2014, available at: http://hearinghealthmatters.org/waynesworld/2014/human-ear-canal-viii/.

* cited by examiner

EAR CLEANING DEVICE WITH PERSONAL AND MEDICAL APPLICATOR USES

CROSS REFERENCES TO RELATED APPLICATIONS

This application is a continuation in part of U.S. application Ser. No. 14/543,450, filed on Nov. 17, 2014, the disclosures of which are incorporated herein by reference.

FIELD OF THE INVENTION

The present invention relates generally to cleaning and applicator devices, and more particularly to a multi-functional swab having a plurality of stick-like stems having an absorbent or nonabsorbent material fixedly attached to the distal ends of the stems.

BACKGROUND OF THE INVENTION

There are other swabs which provide for cleaning and for applying a coating of liquid or powder material. While these swabs may be suitable for the purposes for which they were designed, they would not be as suitable for the purposes of the present invention as heretofore described.

It is thus desirable to provide a multi-functional swab comprising a pair of transversely disposed stick-like handles forming applicator posts, with the terminal ends of the posts having an absorbent or non-absorbent material thereon that can be used to dry or clean a user's ear and ear canal with the transversely disposed applicator post serving as a stop to prevent the over insertion of the swab and where the length of each applicator post is less than the typical distance from the ear canal opening to the tympanic membrane, for infants, toddlers, children and adults.

It is further desirable to provide a multi-functional swab comprising a pair of transversely disposed stick-like handles with the terminal ends having an absorbent or non-absorbent material thereon that can be used to apply a coating to a surface, such as applying medicine or makeup, where each of the absorbent swab heads can have a different color or material thereon, such as eye shadow, rouge, lipstick, etc.

OBJECTS OF THE INVENTION

It is an object of the invention to provide a multi-functional swab having a plurality of transversely disposed stick-like handles with each terminal end having an absorbent or non-absorbent material fixedly attached thereto.

Another object of the present invention is to provide a multi-functional swab that can be used to dry or clean a user's ear and ear canal where each of the swab portions or applicator posts extending from the central transverse junction is of a length that is less than or equal to the typical distance from the ear canal opening to the tympanic membrane.

Yet another object of the present invention is to provide a multifunctional swab having a predetermined length to accommodate use on an infant, toddler, child or adult.

Still yet another object of the present invention is to provide a multi-functional swab having transversely disposed stick-like handles appropriately dimensioned with terminal ends having an absorbent or non-absorbent material thereon that can be used to apply different medical or cosmetic preparations to a user's face, nails, hair, teeth or skin, such as dyes, nail polish, rouge, powders, medicine or the like.

An additional object of the present invention is to provide a multi-functional swab wherein the stick-like handles are manufactured from polymeric, elastomeric, wood or composite materials, as desired.

A further object of the present invention is to provide a multifunctional swab that provides a safer method of drying or cleaning the ear canal since even if a caregiver's hand slips they can not injure the person's ear drum.

A yet further object of the present invention is to provide a multi-functional swab wherein the absorbent or non-absorbent terminal ends are manufactured from fiber, sponge or composite materials, as desired.

A still yet further object of the present invention is to provide a multi-functional swab wherein the transversely disposed stick-like handles optionally provide a gripping portion at the central junction of the transversely disposed applicator posts.

The present invention overcomes the shortcomings of the prior art by providing a multi-functional swab having, in the preferred embodiment, a pair of transversely disposed stick-like stems that serve as four separate applicator posts, each having an absorbent or non-absorbent material fixedly attached to the distal ends. These posts are manufactured with a length less than the average length between an ear canal opening and the tympanic membrane for a user. These different lengths are determined by their intended use for infants, toddlers, children, and adults.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with at least one embodiment of the present invention, an applicator may be particularly configured for use as an ear cleaning device, and the ear cleaning device may be particularly configured for use on two different sized persons. The ear cleaning device may be formed of a pair of posts transversely disposed to intersect each other at a point at substantially a 90 degree angle, being fixedly secured to each other at a selective location on each of the posts, to be substantially coplanar. A first end and a second end of a first post of the pair of posts may each have a swab material secured thereon to form respective first and second swab members, with each of the first and second swab members extending away from the intersection point toward the respective swab materials. A first end and a second end of a second post of the pair of posts may each have a swab material secured thereon to form respective third and fourth swab members, with each of the third and fourth swab members extending away from the intersection point toward the respective swab materials of the second post.

A length of each of the first and second swab members may sized according to a distance from the pinna of the ear to the tympanic membrane for a particular sized person (e.g., an infant); and a length of each of the third and fourth swab members may be sized according to a distance from the pinna of the ear to the tympanic membrane for a second particularly sized person (e.g., a toddler).

The respective swab materials for each of the first and second swab members may be formed to have a first diameter; and the respective swab materials for each of the third and fourth swab members may be formed to have a second diameter, where the first and second diameters are each roughly sized according to the size of the ear canal for the first and second particularly sized persons, respectively (i.e., the first diameter for the first and second swab materials may be sized for the infant, and the second diameter for the third and fourth swab members may be sized for the toddler).

The ear cleaning device may also have a substantially spherical grip portion secured to each of the pair of posts, having a center of the sphere being substantially centered upon the intersection point, to provide a larger surface area to assist the user in gripping of the ear cleaning device.

In another embodiment, a length of the first swab member, a length of the second swab member, a length of the third swab member, and a length of the fourth swab member may each be different, and each may be respectively sized according to a distance from the pinna of the ear to the tympanic membrane for four different sized people. For example, the length of the first swab member may be selected to accommodate the pinna-to-tympanic membrane distance for an infant; the length of the second swab member may be selected to accommodate the pinna-to-tympanic membrane distance for a toddler; the length of the third swab member may be selected to accommodate the pinna-to-tympanic membrane distance for a child; and the length of the fourth swab member may be selected to accommodate the pinna-to-tympanic membrane distance for an adult.

BRIEF DESCRIPTION OF THE DRAWINGS

The description of the various example embodiments is explained in conjunction with appended drawings, in which.

DESCRIPTION OF THE REFERENCED NUMERALS

Turning now descriptively to the drawings, in which similar reference characters denote similar elements throughout the several views, the figures illustrate the use of the present invention. With regard to the reference numerals used, the following numbering is used throughout the various drawing figures:

10 conventional cotton swab;
12 child;
14 conventional cotton swab tip;
16 outer ear;
18 ear canal;
20 tympanic membrane;
22 improved swab;
24 applicator posts;
24A 1st pair transverse posts;
24B 2nd pair transverse posts;
26 center grip portion;
28 applicator tips;
28A 1st pair applicator tips;
28B 2nd pair applicator tips;
30 applicator post intersection;
32 applicator post angle around center;
34 applicator post base;
36 applicator post distal end;
38 tiles;
40 grout;
U user;
100 improved applicator;
101A first swab member;
101AS swab material of the first swab member;
101AD diameter of the swab material of the first swab member;
101B second swab member;
101BS swab material of the second swab member;
101BD diameter of the swab material of the second swab member;
102A third swab member;
102AS swab material of the third swab member;
102AD diameter of the swab material of the third swab member;
102B fourth swab member;
102BS swab material of the fourth swab member;
102BD diameter of the swab material of the fourth swab member;
103 intersection point;
L1 length of the first swab member;
L2 length of the second swab member;
L3 length of the third swab member; and
L4 length of the fourth swab member.

DETAILED DESCRIPTION OF THE INVENTION

As used throughout this specification, the word "may" is used in a permissive sense (i.e., meaning having the potential to), rather than the mandatory sense (i.e., meaning must). Similarly, the words "include", "including", and "includes" mean including but not limited to.

The phrases "at least one", "one or more", and "and/or" are open-ended expressions that are both conjunctive and disjunctive in operation. For example, each of the expressions "at least one of A, B and C", "one or more of A, B, and C", and "A, B, and/or C" mean all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference.

Furthermore, the described features, advantages, and characteristics of any particular embodiment disclosed herein, may be combined in any suitable manner with any of the other embodiments disclosed herein.

Figure 1:
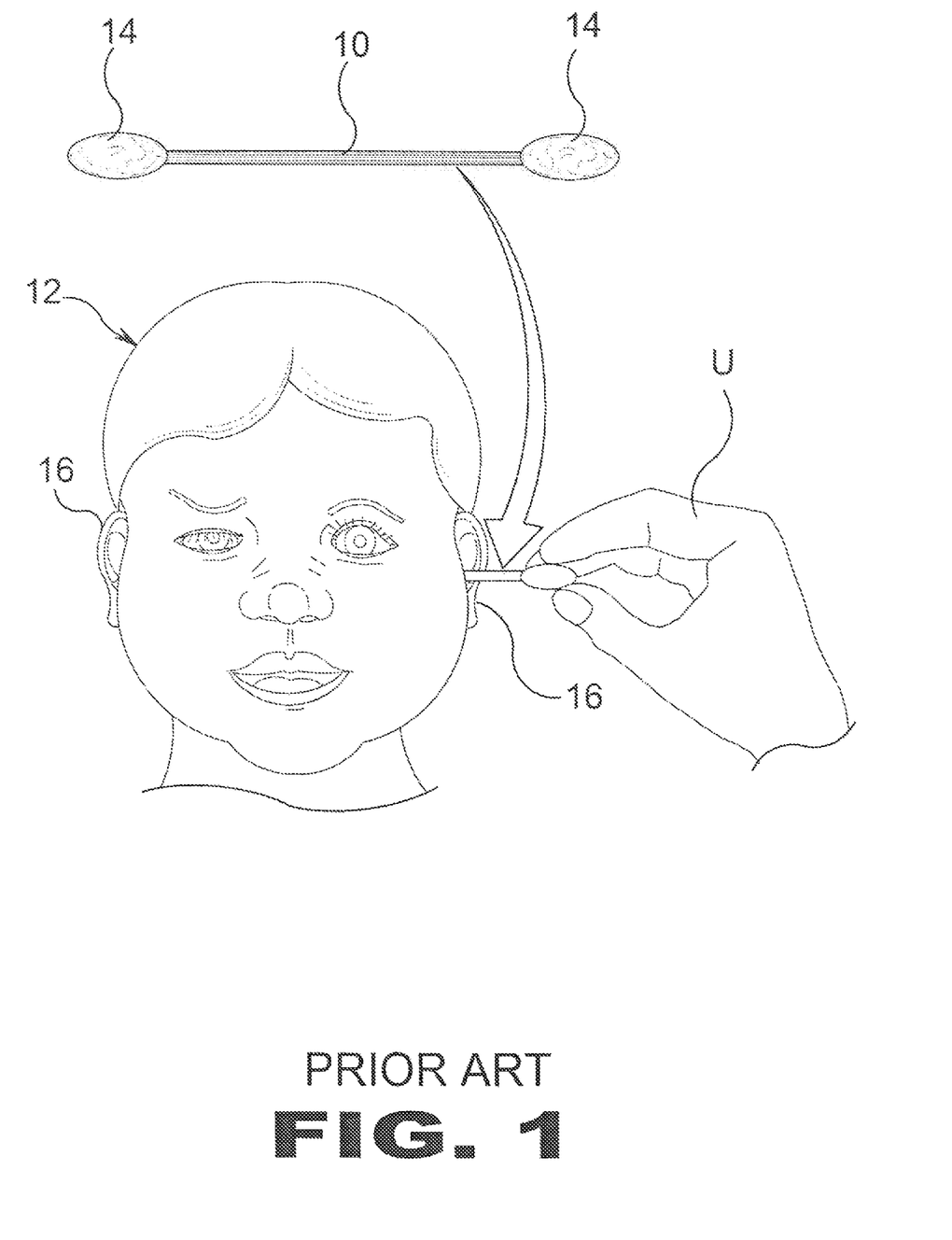
FIG. 1 is a first illustrative view of a prior art swab.

Referring to FIG. 1, shown is an illustrative view of prior art. Conventional cotton swabs (indicated at 10) can potentially be counterproductive or even harmful to the person using them for cleaning the ears of another (such as a child). When people use cotton swab tips they frequently clean out some ear wax, but also push some deeper into the medial canal, pushing it up against the tympanic membrane (ear drum) causing impactions that impair hearing or can lead to infection and pain. Trauma to the ear drum also occurs frequently for those users. When applying medicine or makeup or other personal use items, a user can rotate the device so as to have access to four different applicators. Seen in FIG. 1 is a user U cleaning the ear of a child 12 (only the outer portion is seen in this Figure and is indicated at 16), with a conventional swab 10 having oppositely disposed swab tips at 14. This standard use of the prior art will be compared to the utility of the instant invention and will be discussed below.

Figure 2:
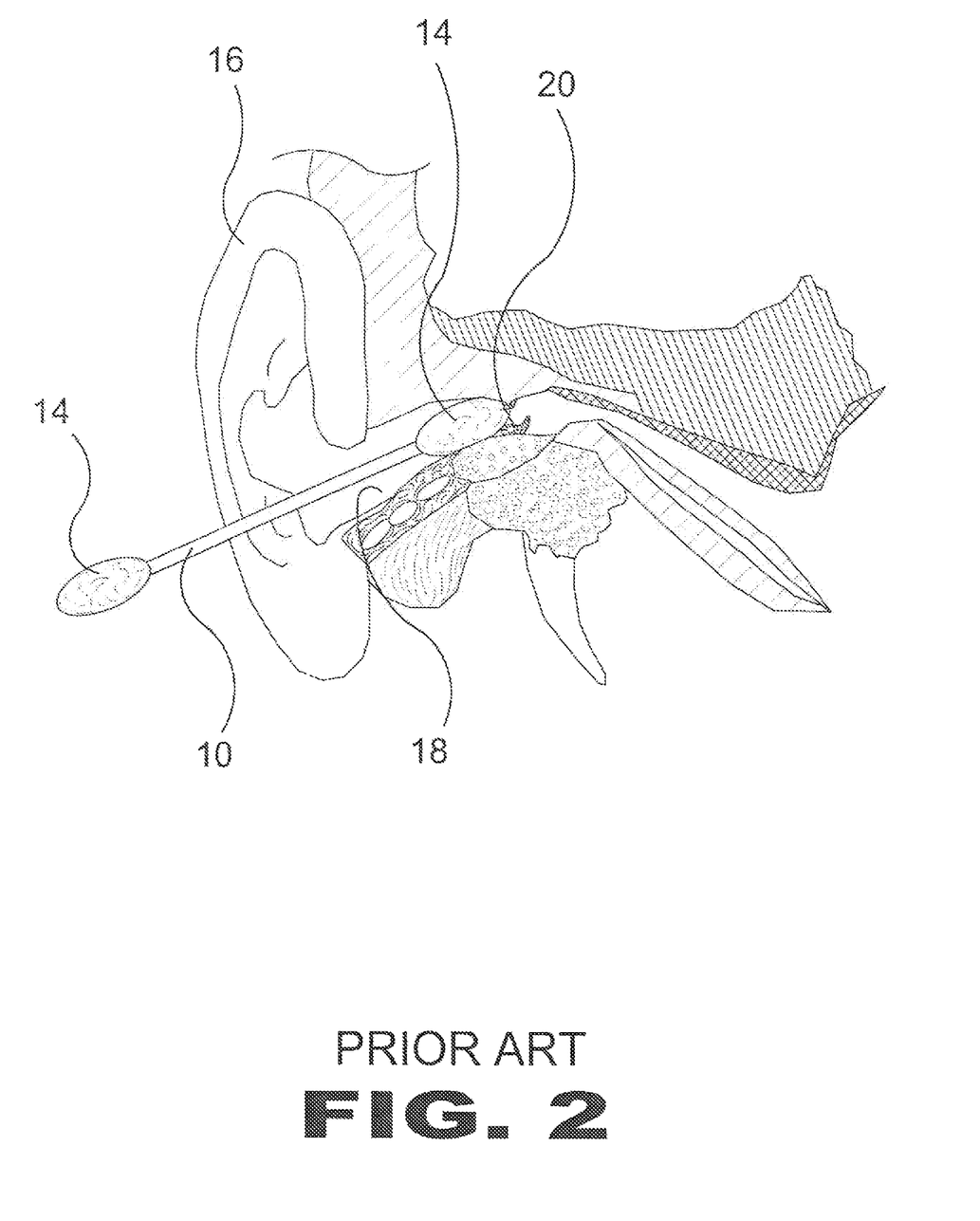
FIG. 2 is a second illustrative view of a prior art swab, shown inserted into the ear canal of a person.

Referring to FIG. 2, shown is an illustrative view of a prior art swab in use. When people use cotton swabs, seen here at 10 with the tips indicated at 14, they frequently clean out some of the ear wax but also push some deeper into the medial ear canal 18, pushing it up against the tympanic membrane (ear drum) 20 causing impactions that can impair hearing, lead to infection, and subsequent pain. Trauma to the ear drum is a real possibility with users of the conventional swab 10 as seen here.

The present invention overcomes these problems by providing a swab tip, with a choice of thickness, having short posts or different lengths for adults (for different uses) that can not penetrate deep into the ear canal and cause damage. This will be explained fully below.

Figure 3:
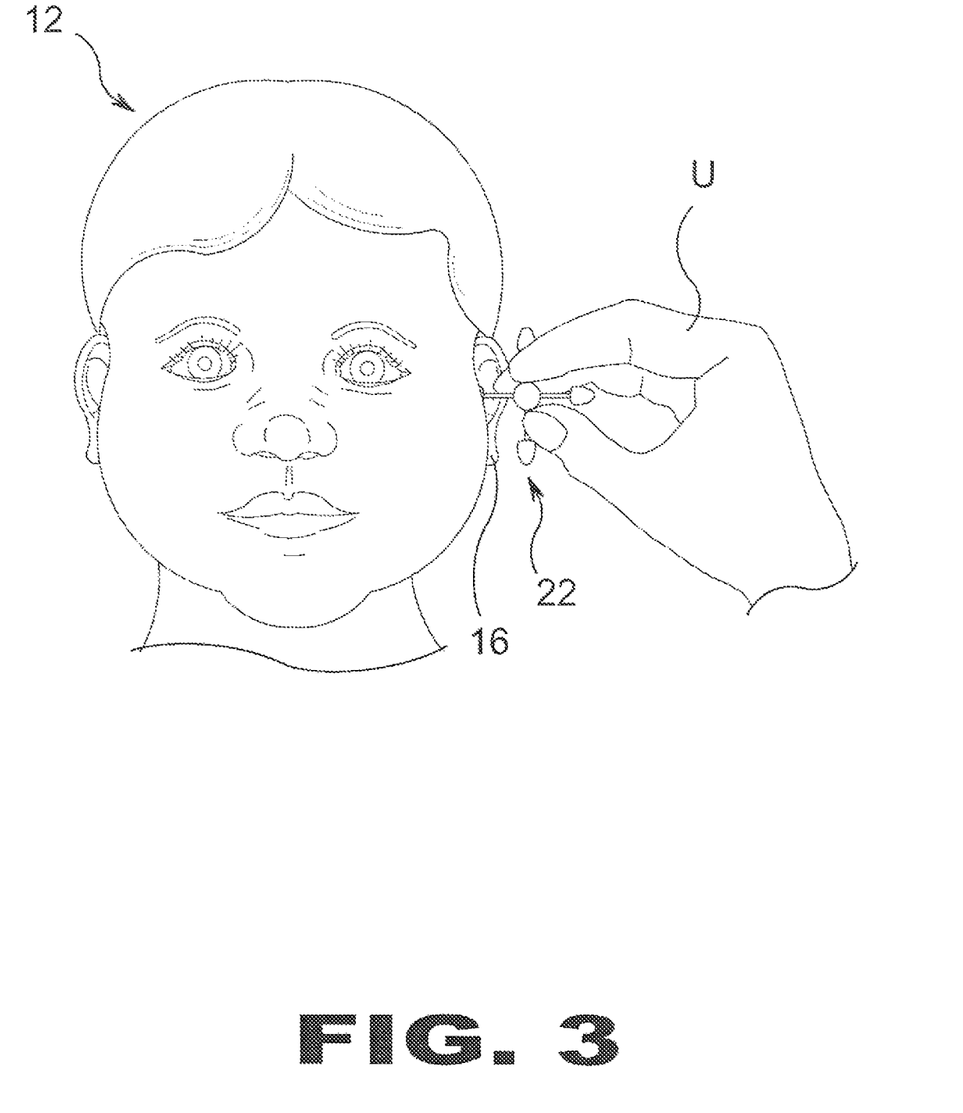
FIG. 3 is an illustrative view of a first embodiment of a swab in accordance with the present invention, shown in use.

Referring now to FIG. 3, shown is an illustrative view of the swab 22 of the present invention in use. Swab 22 may have a plurality of short posts or applicator posts 24 having different lengths, with cotton or other material fixedly attached to each distal end. These are best seen in FIGS. 4 through 8 and will be discussed in detail hereinbelow. The applicator posts 24 are transversely disposed in relation to one another and meet, in one embodiment, in a center grip portion 26. The device is multifunctional and lends itself for many uses including cosmetic use and other personal applications.

Figure 4:
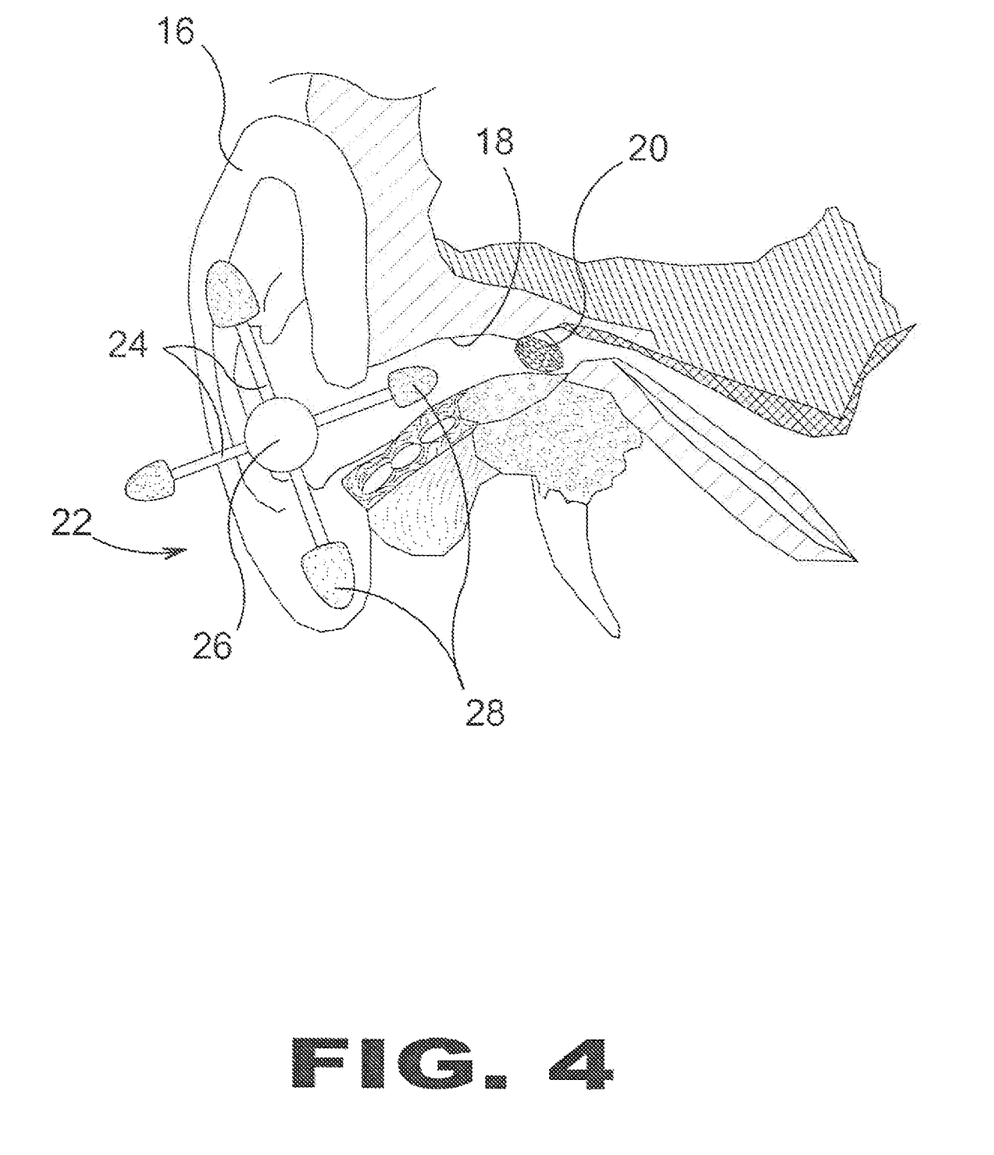
FIG. 4 is a view of the swab of FIG. 3, shown inserted into the ear canal of a person.

Referring to FIG. 4, shown is an illustrative view of the improved swab 22 of the present invention in use. Improved swab 22 includes a plurality of applicator posts indicated at 24. Note that these posts 24 are transversely disposed and radiate from a center portion 26, which in some embodiments of the invention, such as seen here, is made up of a center grip portion 26 that, as can be seen in the Figure, is generally spherical. Other shapes could be used for the purpose, such as cylinders, oblate spheroids, rectangular solids, and the like. Additionally it should be noted that these center portions 26 could be made of various materials, the only common factor being that they should allow the user to easily grip the implement. Also it should be emphasized that the gripping area could be disposed of entirely, simply having the transversely disposed applicator posts 24 cross each other at the center point 26. As aforementioned, the present invention provides a safe productive means for cleaning the exterior of the ear and ear wax buildup without pushing ear wax further and deeper into the ear canal and up against the tympanic membrane, potentially causing damage and loss of hearing. The short post can only enter the ear canal far enough to clean ear wax without damage to the tympanic membrane.

Figure 5:
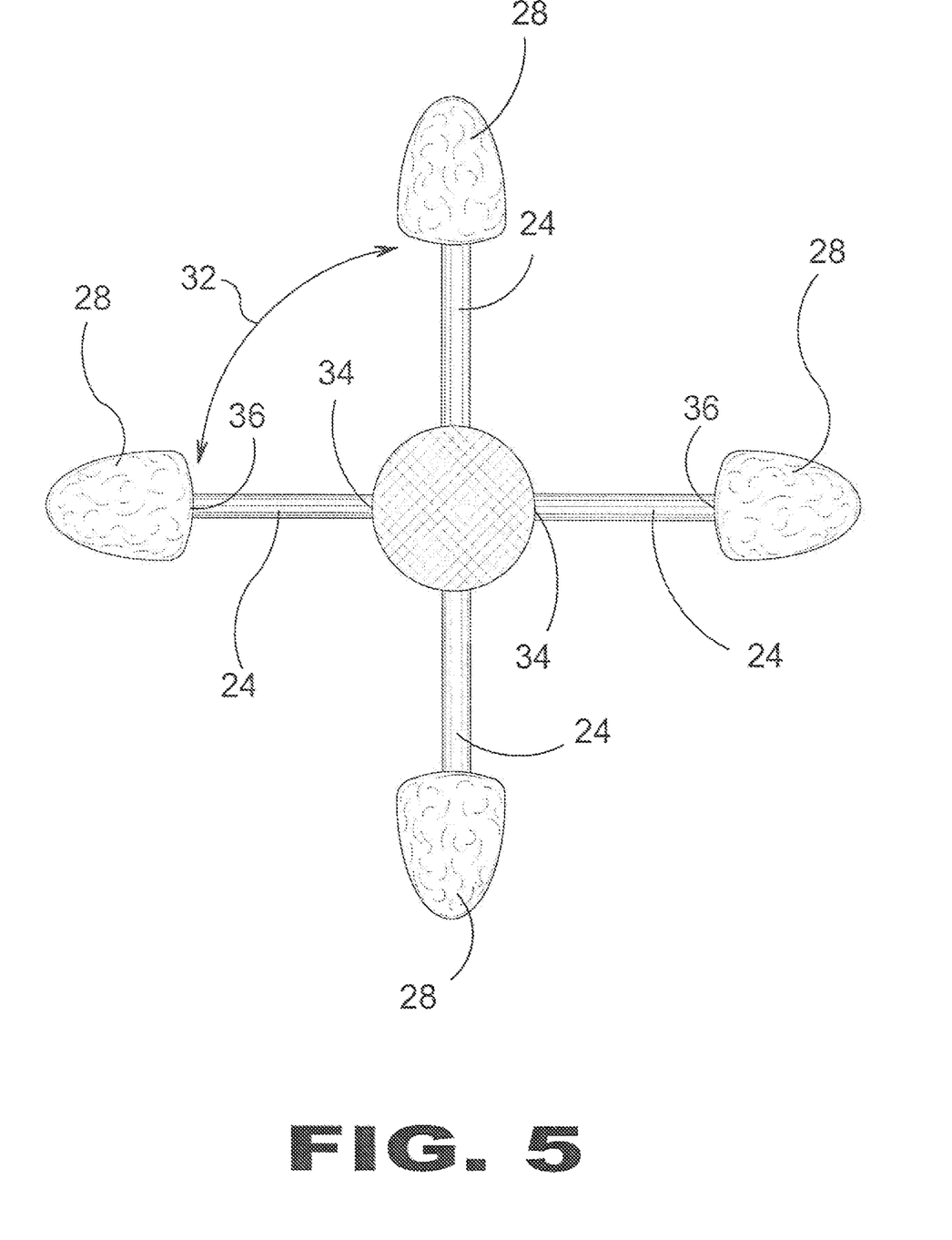
FIG. 5 is a front view of the swab of FIG. 3.

Referring to FIG. 5, more details of the improved swab 22 are shown. Note the applicator posts 24 are clearly seen in the transversely disposed relationship discussed above. Also it should be noted that applicator posts 24 include a applicator post base 34 proximate the center portion 26 and a distal end 36 proximate the applicator tip 28. It should be also noted here that though the posts 24 are shown at a 90° angle to one another and that the phrase "transversely disposed" has been used so far in this description, the angles could be altered without departing from the spirit of the invention in such that the disposition of the pairs of applicator posts will prevent the user or caregiver from inserting the applicator post 24 and its attendant applicator tip 28 beyond a certain predetermined distance into the ear canal 18 being cleaned. This angle between two of the posts is shown in FIG. 5 and is indicated at 32, and it is contemplated that an angle in relation to one another (in regard to the center) would be at least 60°. This feature of the present invention, though, may be achieved through a number of different angles 32 that need not be detailed here. It should also be emphasized that the length of the applicator posts 24 could vary depending on the use for which the improved swab 22 is contemplated, as opposed to the equal lengths throughout as is seen in the Figures. The posts 24 could be made of wood, paper, a polymer, or some combination of these materials; the manufacture depending again on the contemplated use of the improved swab 22.

Figure 6:
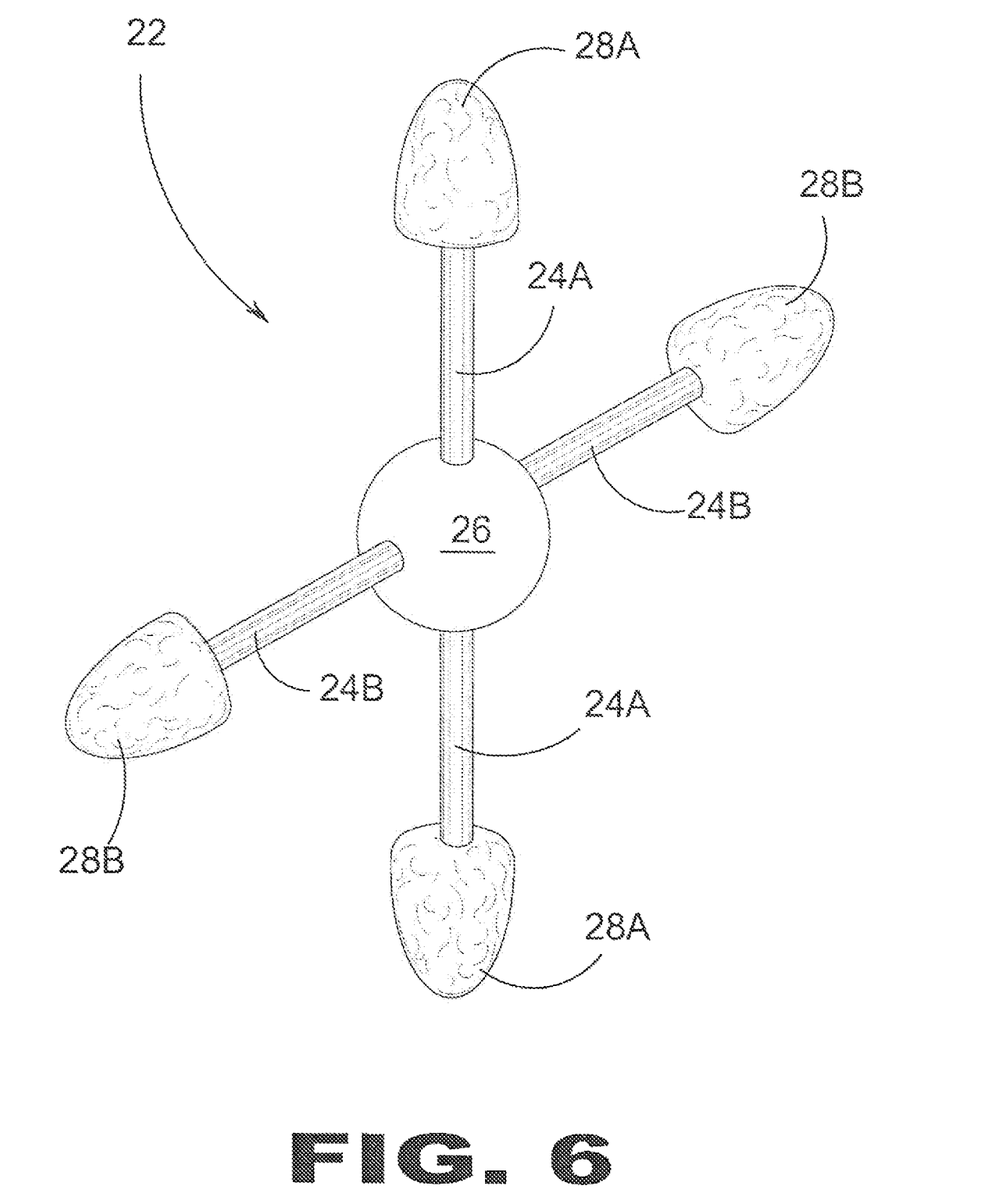
FIG. 6 is a perspective view of the swab of FIG. 3.

Referring to FIG. 6, shown is a perspective view of the swab 22 of the present invention. In this Figure note the pair of applicator posts indicated at 24A and the pair designated 24B. The reason for this dual designation is that in one contemplated embodiment, these two pairs 24A and 24B could have differing lengths. Also seen in this Figure are the applicator pairs 28A and 28B. The reason for these designated pairs in the Figure is that in certain contemplated embodiments, the size of the applicators (generally designated at 28) could differ one from the other according to the use needed. Returning to the differing lengths of application posts 24, it is known that the distance in an adult from the pinna (outer ear) to the tympanic membrane (eardrum) is approximately 2.5 cm.

It has been reported that by the pre-teen age, the ear canal typically reaches the adult size. See, Hearing Health & Technology Matters, Wayne's World, Human Ear Canal VIII, Jul. 28, 2014, available at: http://hearinghealthmatters.org/waynesworld/2014/human-ear-canal-viii/.

More specifically, research in this area has shown that the ear canal length in infants increases from 0.3 cm (3 millimeters) to 1.1 cm (11 millimeters), with increasing age up to 6 months. See, Carolina Abdula and Douglas H. Keefe, Human Auditory Development, Chap. 2, Morphological and Functional Ear Development, pp. 22-24; and Fred H. Bess and Judith S. Gravel, Foundations of Pediatric Audiology, Plural Publishing, Inc., 2006, p. 299.

It is reported that a majority of the changes in the ear canal length occur between the ages of 6 months and 12 months. See, Fred H. Bess and Judith S. Gravel, Foundations of Pediatric Audiology, Plural Publishing, Inc., 2006, p. 299.

The ear canal length may reach 1.68 cm (16.8 mm) during infancy (i.e., up to 1 year old). See, Human Auditory Development, p. 20; and Functional Anatomy of the Newborn, Edmund S. Crenlin, 1973, New Haven and London: Yale University Press.

In general, adult female ear canals tend to be shorter than those of males by about 1 to 3.7 mm. See, Hearing Health & Technology Matters, Wayne's World, Tympanic Membrane-Anatomical Influence on Hearing and Fittings, Apr. 23, 2013, http://hearinghealthmatters.org/waynesworld/2013/tympanic-membrane-anatomical-influence-on-hearing-aid-fittings/.

See, also: Salvinelli, F., Maurizi, M., Calamita, S., D'Alatri, L., Capelli, A., and Carbone, A, 1991, Scandinavian Audiology, 20, 253-256; Staab, W., Deep canal Hearing Aids: Theory and practice," ASHA Miniseminar, New Orleans, La., November 1994; Oliviera, R. The Dynamic Ear Canal, Chapter 6, The Human Ear Canal, Ballachanda (Ed), Singular Publishing Group, Inc., San Diego, 1995 pp. 84-111; Bezold, F. *Die Corrosions-Anatomie des Ohres*, 1882; Chan, J., and Giesler, C., 1980, Estimation of Eardrum Acoustic Pressure and of Ear Canal Length from Remote Points in the Canal, *Journal of the Acoustical Society of America*, 87(3), 1237-1247; Zemplenyi, J., Gilman, S., and Dirks, D., 1985, Optical Method for Measurement of Ear Canal Length, *Journal of the Acoustical Society of America*, 78, 2146-2148; Djupesland, G., and Zwislocki, J., 1972, Sound Pressure Distribution in the Outer Ear, Scandinavian Audiology, 4, 197-203; von Békésy, G., 1960, *Experiments in Hearing*, New York, McGraw-Hill; and Wiener, G., and Ross, D., The Pressure Distribution in the Auditory Canal in a Progressive Sound Field, J. Acoust. Soc. Amer., 1946, 18, 401-408.

More data regarding ear canal length is available from impressions made on cadavers than data from living patients, which is nonetheless indicative of such lengths for living humans. See, Hearing Health & Technology Matters, Wayne's World, Tympanic Membrane-Anatomical Influence on Hearing and Fittings, Cadaver v. Living Ear Measurements; and Smelt, G., Hawke, M. and Proops, D, 1988, Anatomy of the external ear canal: a new technique for making impressions, The Journal of Otolaryngology, 17, 249-253. Such data shows that the ear canal length for adult males generally falls between 22.6 mm and 27.8 mm, while the ear canal length for the females generally falls between 20.2 mm and 24.8 mm.

It can be seen then that the instant invention can be made in varying sizes according to the age of the infant or child. Again it should be noted that additionally the transverse posts 24A, 24B could all be of different lengths to allow a single one of the improved swabs 22 to be used in a variety of age-related circumstances.

Figure 7:
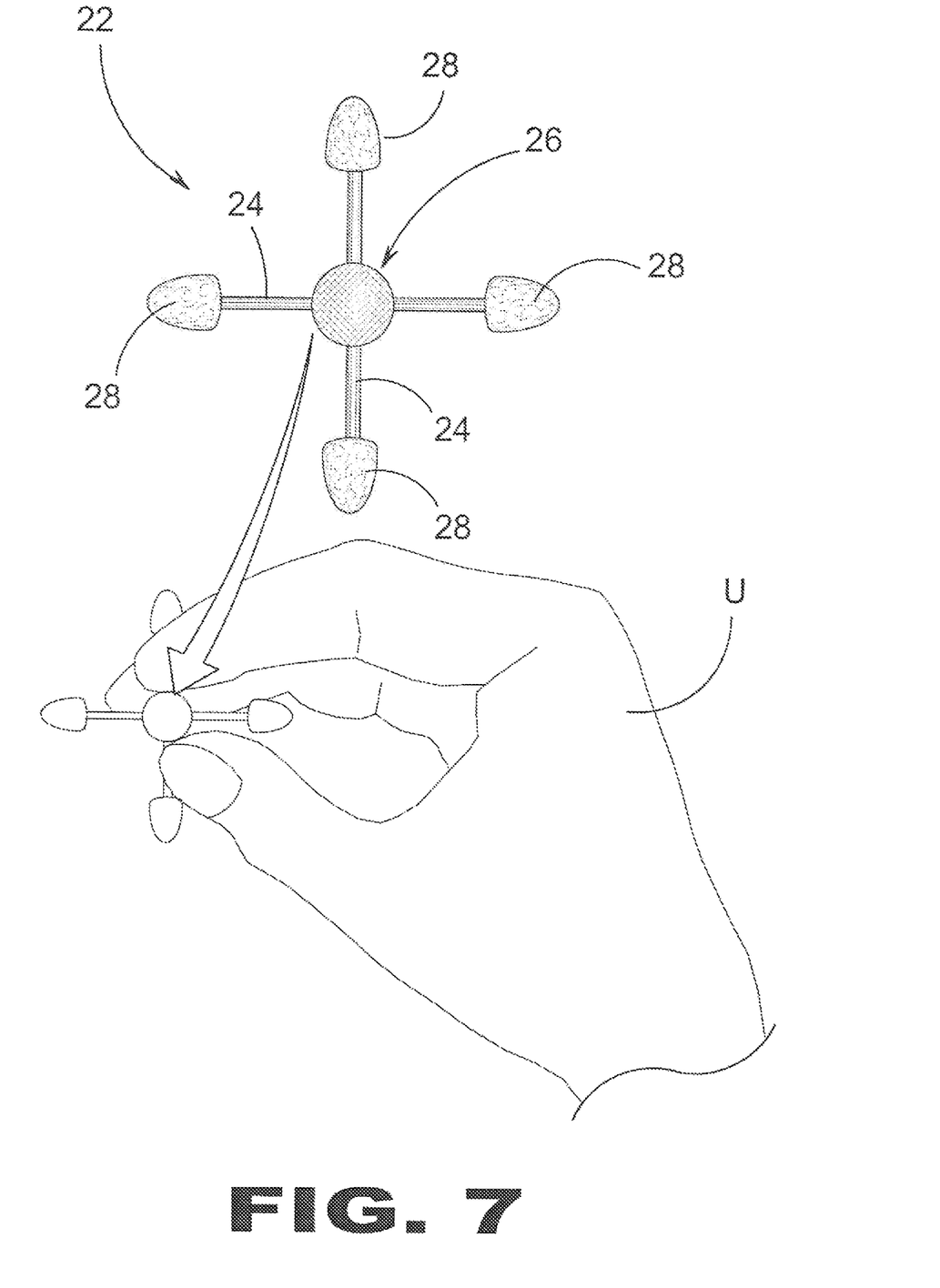
FIG. 7 is a perspective view that illustrates a user grasping the spherical grip portion of the swab of FIG. 3.

Referring to FIG. 7, shown is a perspective view of the present invention with a user U engaging the center grip portion 26. As mentioned above, the center grip portion 26 could be made of a variety of materials and be configured in a variety of shapes. It could be made of a memory material that conforms to the user's grip or be made of a static material, either compressible or non-compressible. Alternatively and, also as mentioned above, it could simply be the intersection point of the two transversely disposed applicator posts 24A and 24B (as seen in FIG. 6). Turning to the actual applicator tips 28 these could be made of a variety of materials, depending on the use for which the improved swab 22 is intended. Cotton, foam rubber (of diverse densities and hardness, or many other pliant and/or absorbent or non-absorbent material could be used. As noted above the applicator tips 28 could be of varying sizes and, along with varying materials, could be combined in the same unit (improved swab 22) to allow for multiple uses: earwax removal, makeup application, or the cleaning of small objects, or working with glue or other solvents to administer or clean crevices, for example.

Figure 8:
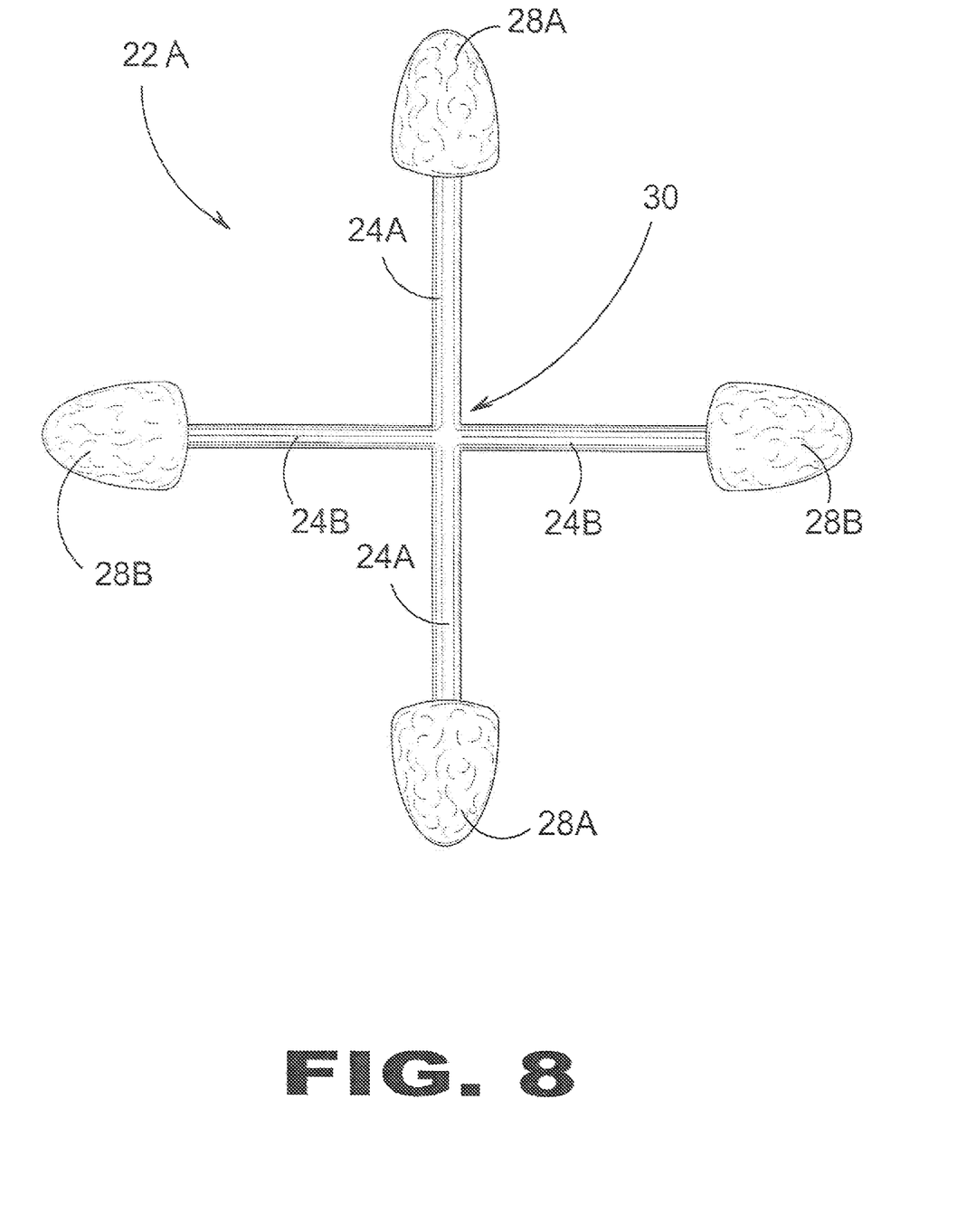
FIG. 8 is a front view of a second embodiment of a multi-tip swab formed in accordance with the present invention.

Referring to FIG. 8, an embodiment of the present invention indicated at 22A is seen without the center grip portion 26 shown in the above Figures, as it is replaced by the applicator post intersection 30, which serves the same all-around function. The applicator posts 24A and 24B for swab 22A may similarly be made of various materials depending on the use for which the improved swab 22A is to be used. The same applies to the applicator tips 28A and 28B.

Figure 9:
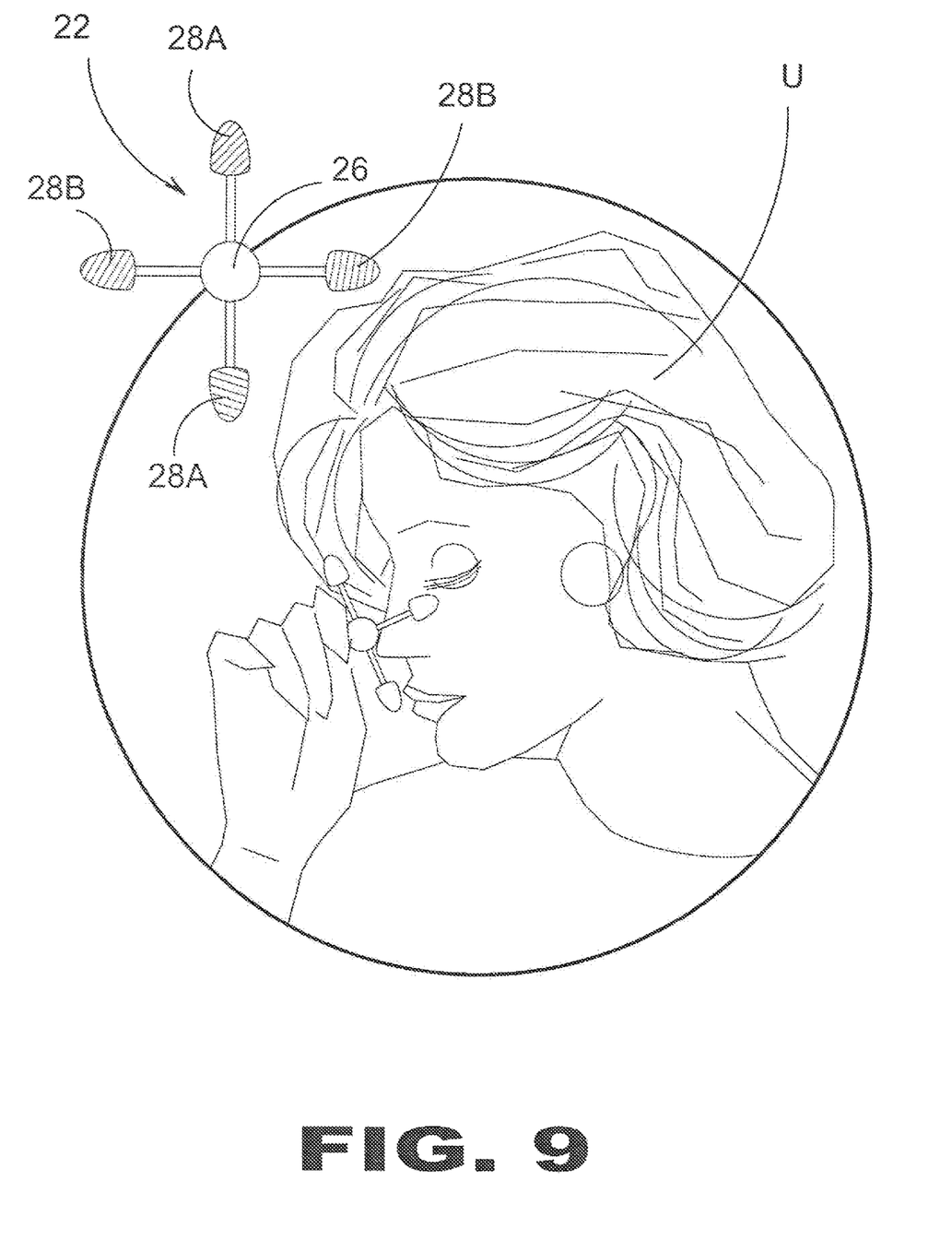
FIG. 9 is an illustrative view of the swab of FIG. 3 shown in use for applying makeup.

Referring to FIG. 9, shown is an illustrative view of the swab 22 in use for applying makeup. The device provides a safe productive means for applying four different colors of make-up, eye shadow and liner and by using and reusing the four applicators less make-up and swabs will be used, saving money and giving the individual faster and greater control of the cosmetics.

Figure 10:
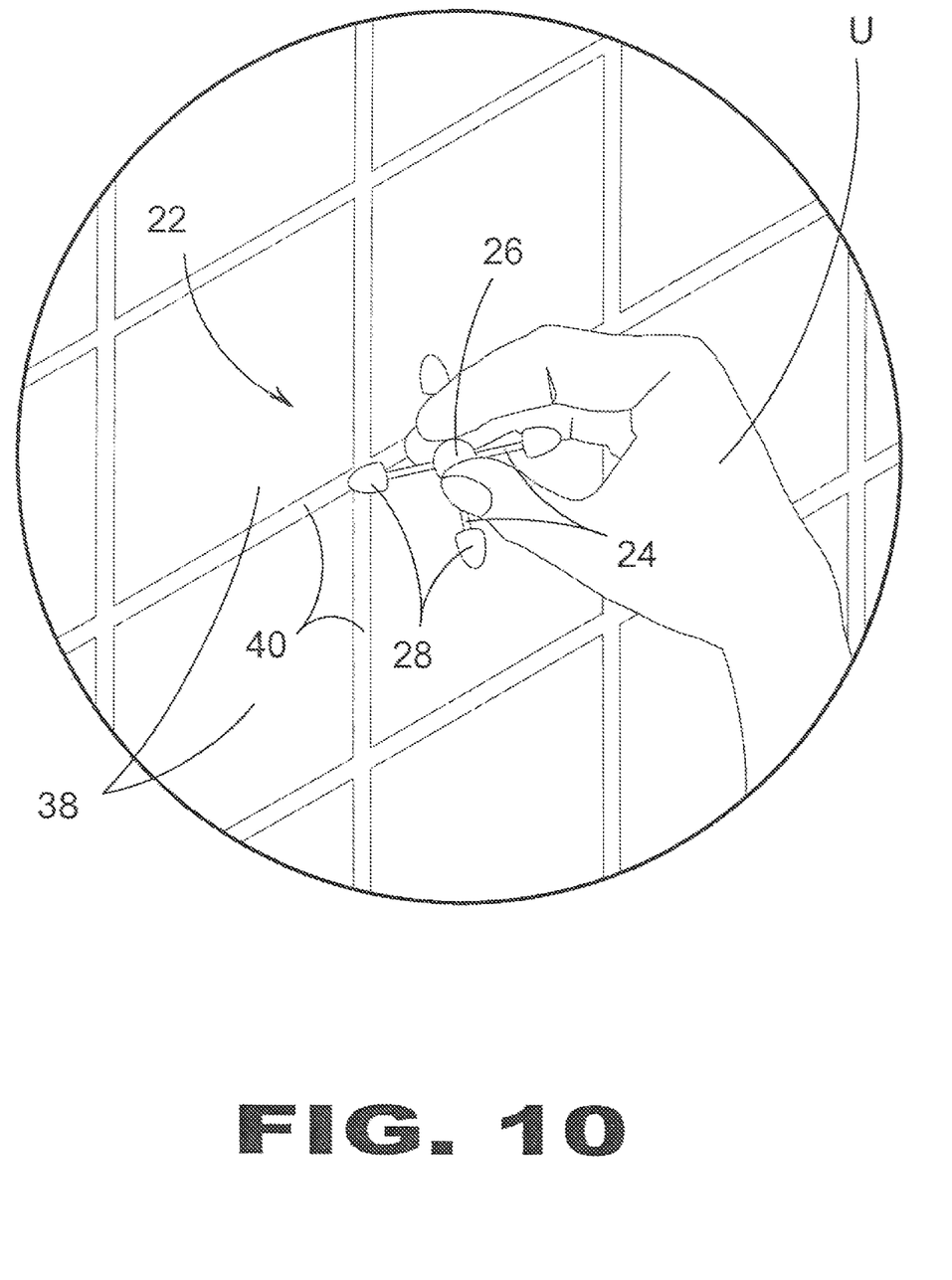
FIG. 10 is an illustrative view of the swab of FIG. 3 shown in use for cleaning grout.

Referring to FIG. 10, shown is the swab 22 having a plurality of applicator posts with cotton or other material fixedly attached thereto. The device is multifunctional and as shown, can be used to clean the grout 40 between tiles 38 or to apply cleaning agents or solvents to a workpiece. The posts 24 could be made of wood, paper, a polymer, or some combination of these: the manufacture depending again on the contemplated use of the improved swab 22 with the applicator tips 28 of varying sizes and/or varying materials, to allow for multiple uses including cleaning of small objects, or working with glue or other solvents or clean crevices.

Figure 11:
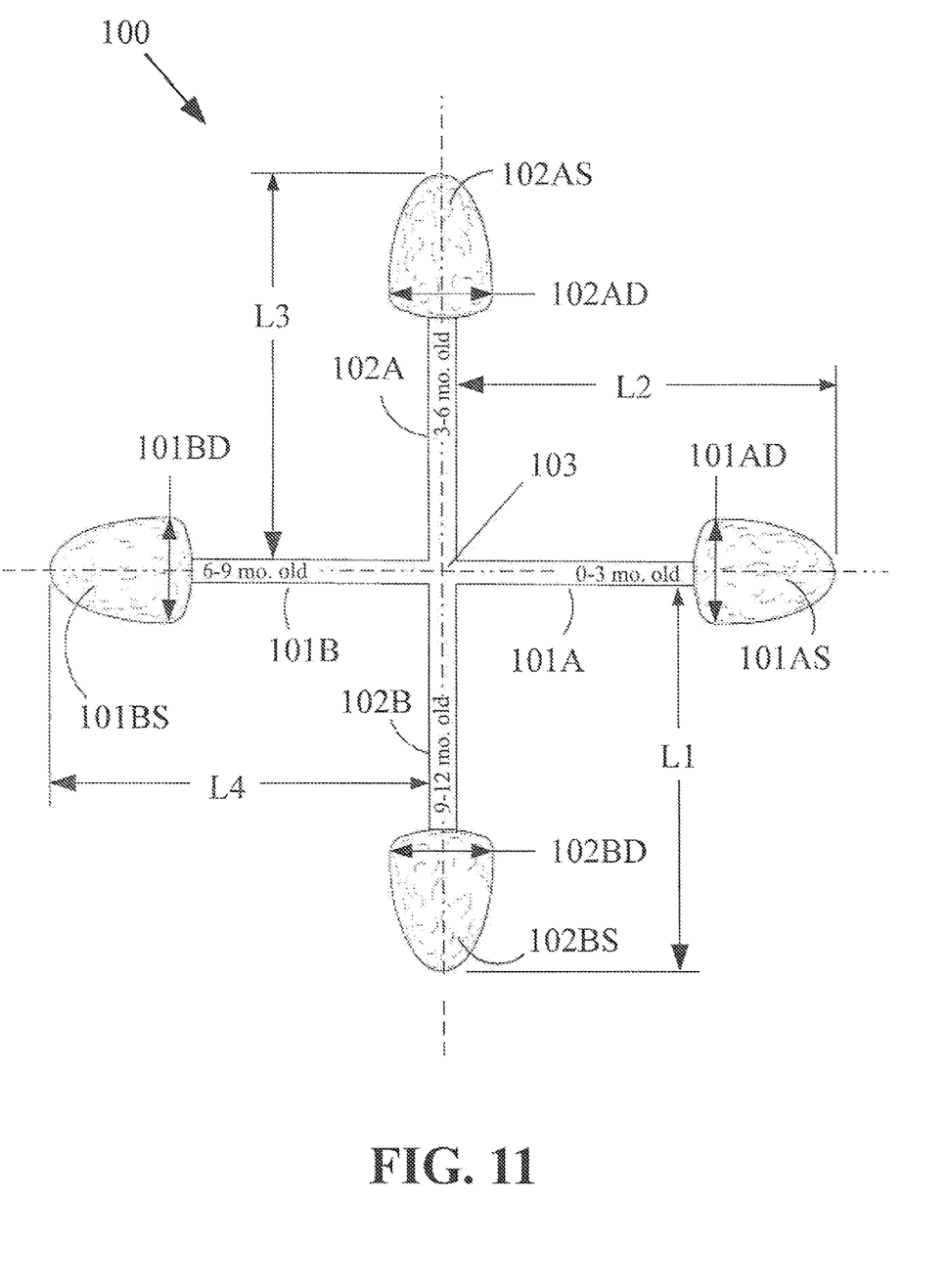
FIG. 11 is a front view of another embodiment of a multi-tip swab formed in accordance with the present invention.

Similar to the aforementioned embodiments, the applicator 100 illustrated within FIG. 11 may have the axis of a first member intersect the axis of a second member at a point 103, at substantially a 90 degree angle, for the first member to form a first swab member 101A and a second swab member 101B, and for the second member to form a third swab member 102A and a fourth swab member 102B. The first member and second members may each be formed to have a circular cross-section, or other any suitable cross-section (e.g., a square shaped cross-section), and the axes may be formed to be coplanar, within ordinary manufacturing tolerances. The first member and second members may each be formed to be rigid, and to not be very flexible, or even flexible at all during normal handling by a person's hand, which rigidity is in part a natural occurrence of the support that is provided by the ninety degree arrangement (i.e., each member/post has an effective length that is shortened by 50% as it is cantilevered from the other member oriented at 90 degrees thereto); however, the first member and second members may each be formed to be rigid enough so as to not deflect more than one-half of a millimeter at the distal end, when a normal handling load (e.g., less than one-half of a pound in one embodiment, and less than one or two pounds in other respective embodiments) is applied to the applicator for insertion into the person's ear canal. The distal ends of the swab members 101A, 101B, 102A, and 102B may respectively have swab materials 101AS, 101BS, 102AS, and 102BS secured thereto, being formed with respective maximum outer diameters 101AD, 101BD, 102AD, and 102BD.

Figure 12:
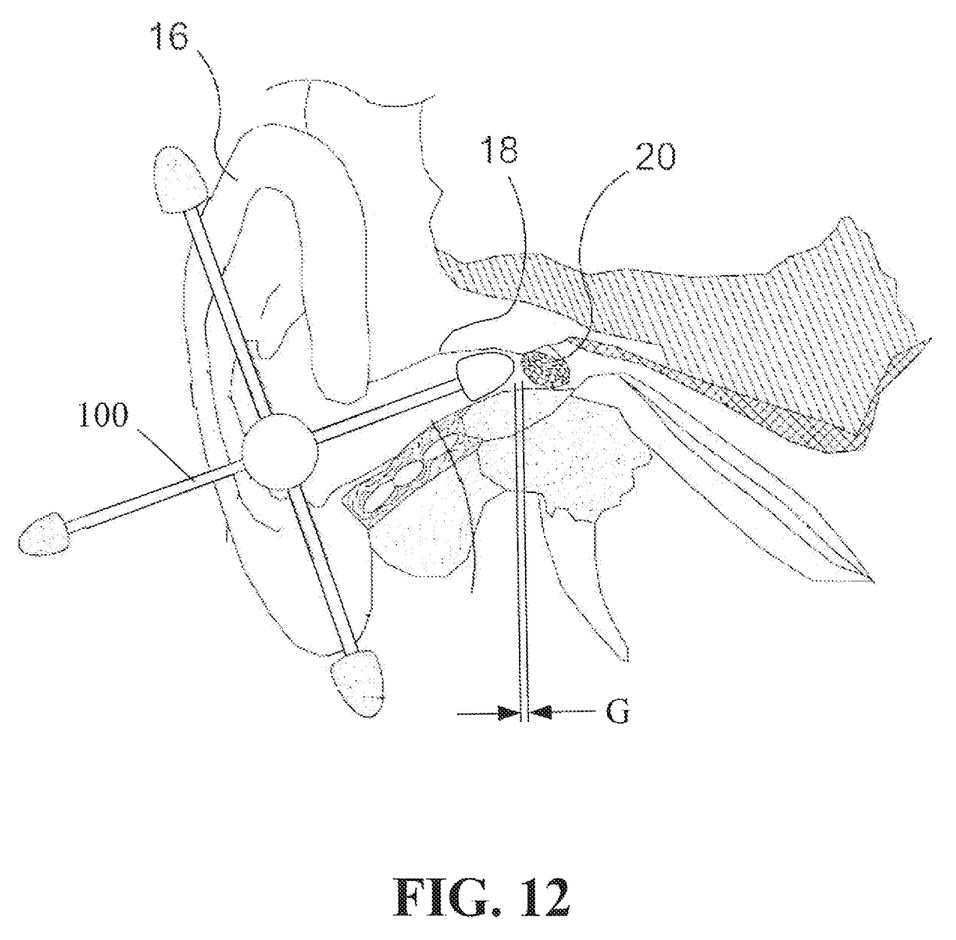
FIG. 12 is a view of the swab of FIG. 11, shown inserted into the ear canal of a person.

The respective lengths L1, L2, L3, and L4 for the swab members 101A, 101B, 102A, and 102B may each be the same in one embodiment (i.e., L1=L2=L3=L4). That singular length may be particularly sized so as to leave a small gap G between the swab material at its distal end and the tympanic membrane, when the side of the perpendicular member rests against the pinna of the ear, as shown in FIG. 12.

In another embodiment, each of the lengths L1, L2, L3, and L4 for the swab members 101A, 101B, 102A, and 102B may be uniquely different (i.e., L1≠L2; L1≠L3; L1≠L4; L2≠L3; L2≠L4; and L3≠L4). For example, as noted above, the length L1 may be sized for an infant, the length L2 may be sized for a toddler, the length L3 may be sized for a child, and the length L4 may be sized for an adult. For example, in one embodiment, L1 may be in the range of 3 mm to 16.8 mm; L2 may be in the range of 16.9 mm to 20 mm; L3 may be in the range of 20 mm to 22 mm; and L4 may be in the range of 22 mm to 28 mm. In another embodiment, the lengths for L1, L2, L3, and L4 may respectively fall in particular ranges, which may be the ranges cited in any example disclosed herein plus a constant added to each, which constant may account for the clocking that the perpendicular member rests against the pinna of the ear, which structure varies around the periphery of the ear (i.e., the pinna is neither symmetric nor regularly shaped). The constant may be a percentage of the ear canal length (i.e., 5% to 15% of the ear canal length, or 15% to 25%, or 25% to 35%). In yet another embodiment, the lengths for L1, L2, L3, and L4 may be unique and particularly sized to only accommodate an infant (i.e., up to one year old); thus L1 may be in the range of 3 mm to 6.5 mm; L2 may be in the range of 6.6 mm to 11.0 mm; L3 may be in the range of 11.1 mm to 13.6 mm; and L4 may be in the range of 13.7 mm to 16.8 mm. For ease of identification by the user, each of the swab members for any embodiment disclosed herein may have markings thereon, and exemplary marking are shown in FIG. 11 (i.e., "0-3 mo. old" and "3-6 mo. old" and "6-9 mo. old" and "9-12 mo. old"). As it may be difficult for some users to read the markings, each of the swab members may color coded to indicate increasing length. For example, the post of the shortest length swab member may be a light yellow color, the post of the next longest swab member may be colored a noticeably darker shade of yellow, the shaft of the third longest swab member may be colored an even darker shade of yellow, while the post of the longest length swab member may be the darkest yellow color. The increasingly darker yellow colors/shades may serve to advise increasing caution because of the longer lengths.

However, the overall size of the ears of an infant tend to be very small as compared to the ear size of an adult, and the infant ear sizes also vary somewhat. See, Yakov Sivan, Paul Merlob, and Salomon H Reisner, Assessment of Ear Length and Low Set Ears in Newborn Infants, Journal of Medical Genetics, 1983, 20, 213-215. Moreover, the ratio of the swab length required to reach and be proximate to the tympanic membrane to the length of the pinna of the ear may be disparate. Therefore, to accommodate the differences in ear size, and to better accommodate proper usage of the applicator by having the perpendicular member properly resting against the side of the pinna of the ear, at least for the infant, for which the length is critical, as an adult may sense when the swab contacts the ear drum, another embodiment of the present invention may have one pair of lengths (e.g., L1 and L3) sized for an infant and one pair of lengths (e.g., L2 and L4) sized for an adult. In one version of this embodiment, the lengths for L1 and L2 may be sized in the range of 3 mm to 6.5 mm to be usable for an infant roughly up to 3 months old, while L3 and L4 may each be in the range of 20 mm to 25 mm to be usable for an adult female. Thus, a caregiving mother of a newborn infant may use the two swab members with lengths L1 and L2 to clean her infant's ears, and may subsequently use the two swab members with lengths L3 and L4 to clean her own ears, and may then dispose of the applicator. Other versions may also be similarly formed and marketed, such as the same version for both infants and the adult female, but where the lengths for L1 and L2 may be sized in the range of 6.6 mm to 11 mm to be usable for an infant roughly between 3 months and 6 months of age; or where the lengths for L1 and L2 may be sized in the range of 11.1 mm to 13.6 mm to be usable for an infant roughly between 6 months and 9 months of age; or where the lengths for L1 and L2 may be sized in the range of 13.7 mm to 16.8 mm to be usable for an infant roughly between 9 months and 12 months of age. Similarly, another version may be formed where the lengths for L1 and L2 may be sized for any of the above-mentioned ranges for an infant, and where the lengths L3 and L4 may each be in the range of 23 mm to 28 mm to be usable for an adult male. Also, a version may be similarly formed where the lengths for L1 and L2 may be sized for any of the above-mentioned ranges for an infant, and the length L3 may be in the range of 20 mm to 25 mm to be usable for an adult female, and the length L4 may be in the range of 23 mm to 28 mm to be usable for an adult male.

While illustrative implementations of one or more embodiments of the present invention are provided hereinabove, those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. An ear cleaning device configured for use on two different sized persons, said ear cleaning device comprising: a pair of posts transversely disposed to intersect each other at a point at substantially a 90 degree angle to each other, being fixedly secured to each other at a selective location on each of said posts, to be substantially coplanar, a first end and a second end of a first post of said pair of posts each having a swab material secured thereon to form respective first and second swab members, with each of said first and second swab members extending away from said intersection point toward said respective swab materials; a first end and a second end of a second post of said pair of posts each having a swab material secured thereon to form respective third and fourth swab members, with each of said third and fourth swab members extending away from said intersection point toward said respective swab materials of said second post; wherein a length of each of said first and second swab members is sized according to a distance from the pinna of the ear to the tympanic membrane for a first person having an ear comprising a first size; and wherein a length of each of said third and fourth swab members are sized according to a distance from the pinna of the ear to the tympanic membrane for a second person having an ear comprising a second size; and a roughly spherical center grip portion secured to each of said pair of posts and being substantially centered upon said intersection point, to provide a larger surface area to assist in gripping said ear cleaning device.

2. The ear cleaning device as claimed in claim 1 wherein each of said first and second swab members are formed to be substantially rigid with respect to said third and fourth swab members; and wherein each of said third and fourth swab members are formed to be substantially rigid with respect to said first and second swab members.

3. The ear cleaning device as claimed in claim 2 wherein said length of said first swab member, said length of said second swab member, said length of said third swab member, and said length of said fourth swab member are each formed to be a uniquely different length.

4. The ear cleaning device as claimed in claim 2 wherein said length of each of said first and second swab members is sized according to said distance from the pinna of the ear to the tympanic membrane for an infant; and wherein said length of each of said third and fourth swab members are sized according to said distance from the pinna of the ear to the tympanic membrane for an adult female.

5. The ear cleaning device as claimed in claim 4 wherein said length of each of said first and second swab members is sized according to said distance from the pinna of the ear to the tympanic membrane for an infant up to the age of three months.

6. The ear cleaning device as claimed in claim 2 wherein said length of said first swab member is sized according to said distance from the pinna of the ear to the tympanic membrane for an infant up to the age of three months; wherein said length of said second swab member is sized according to said distance from the pinna of the ear to the tympanic membrane for an infant between the age of three months and six months; wherein said length of said third swab member is sized according to said distance from the pinna of the ear to the tympanic membrane for an infant between the age of six months and nine months; and wherein said length of said fourth swab member is sized according to said distance from the pinna of the ear to the tympanic membrane for an infant between the age of nine months and twelve months.

7. The ear cleaning device as claimed in claim 2 where said swab material for each of said first and second swab members is a first thickness; and where said swab material for each of said third and fourth swab members is a second thickness, said second thickness being different than said first thickness.

8. The ear cleaning device as claimed in claim 2 where each said post is made of a material from the group of materials consisting of: a polymeric material, and paper.

9. The ear cleaning device as claimed in claim 2 where at least one of said first, second, third, and fourth swab members are made of an absorbent material, and at least one is made of a non-absorbent material.

10. The ear cleaning device as claimed in claim 2 where at least one of said first, second, third, and fourth swab members are made of cotton, and at least one is made of a non-cotton material.

11. The ear cleaning device as claimed in claim 2 where said swab material is made of foam rubber.

12. The ear cleaning device as claimed in claim 2 where each said post is made of a polymeric material and where said swab material is cotton.

13. The ear cleaning device as claimed in claim 2 where each said post is made of wood and where said swab material is made of cotton.

14. The ear cleaning device as claimed in claim 2 where each said post is made of paper and where each said swab material is made of cotton.

15. An ear cleaning device configured for use on a plurality of different persons, said ear cleaning device comprising: at least a first post and a second post, transversely disposed to intersect each other at a point at substantially a 90 degree angle, and fixedly secured to each other at a selective location of each of said at least two posts to be substantially coplanar; a first end and a second end of said first post each having a swab material secured thereon to form respective first and second swab members, with each of said first and second swab members extending away from said intersection point toward said respective swab materials of said first post; and a first end and a second end of said second post each having a swab material secured thereon to form respective third and fourth swab members, with each of said third and fourth swab members extending away from said intersection point toward said respective swab materials of said second post; and wherein a length of said first swab member, said second swab member, said third swab member, and said fourth swab member is sized according to a distance from the pinna of the ear to the tympanic membrane, for an infant, for a toddler, for a child, and for an adult, respectively; and a roughly spherical center grip portion secured to each of said pair of posts and being substantially centered upon said intersection point, to provide a larger surface area to assist in gripping said ear cleaning device.

16. The ear cleaning device as claimed in claim 15 where said swab material for each of said first and second swab members is a first thickness; and where said swab material for each of said third and fourth swab members is a second thickness, said second thickness being different than said first thickness.

* * * * *